US00PP17124P3

(12) United States Plant Patent
Beineke

(10) Patent No.: US PP17,124 P3
(45) Date of Patent: Oct. 3, 2006

(54) BLACK WALNUT TREE NAMED 'BEINEKE 13'

(50) Latin Name: ***Juglans nigra* L.**
Varietal Denomination: Beineke 13

(75) Inventor: Walter F. Beineke, West LaFayette, IN (US)

(73) Assignee: American Forestry Technologies, Inc., West Point, IN (US)

( * ) Notice: Subject to any disclaimer, the term of this patent is extended or adjusted under 35 U.S.C. 154(b) by 25 days.

(21) Appl. No.: 10/888,759

(22) Filed: Jul. 9, 2004

(65) Prior Publication Data

US 2006/0010538 P1 Jan. 12, 2006

(51) Int. Cl.
*A01H 5/00* (2006.01)

(52) U.S. Cl. ..... Plt./154
(58) Field of Classification Search ..... Plt./154
See application file for complete search history.

(56) References Cited

U.S. PATENT DOCUMENTS

| | | | |
|---|---|---|---|
| PP4,132 | P | 10/1977 | Genn |
| PP4,388 | P | 2/1979 | Forde |
| PP4,389 | P | 2/1979 | Forde |
| PP4,405 | P | 4/1979 | Forde |
| PP4,542 | P | 6/1980 | Beineke |
| PP4,543 | P | 6/1980 | Beineke |
| PP4,614 | P | 1/1981 | Beineke |
| PP4,954 | P | 11/1982 | Beineke |
| PP4,955 | P | 11/1982 | Beineke |
| PP4,964 | P | 12/1982 | Beineke |
| PP4,966 | P | 12/1982 | Beineke |
| PP4,968 | P | 12/1982 | Beineke |
| PP4,971 | P | 1/1983 | Beineke |
| PP6,973 | P | 8/1989 | Madison |
| PP9,906 | P | 6/1997 | Jones |
| PP9,924 | P | 6/1997 | Jones |
| PP9,925 | P | 6/1997 | Jones |
| PP14,777 | P2 | 5/2004 | Beineke |
| PP14,829 | P2 | 5/2004 | Beineke |
| PP14,839 | P2 | 6/2004 | Beineke |
| PP14,978 | P2 | 7/2004 | Beineke |
| PP15,079 | P2 | 8/2004 | Beineke |

OTHER PUBLICATIONS

Appleton, Bonnie, et al. (2000) "Trees for problem Landscape Sites—The Walnut Tree: Allelopathic Effects and Tolerant Plants" *Virginia State University* Publication No. 430–021.
Beineke, Walter F. (1989) "Twenty Years of Black Walnut Genetic Improvement at Purdue University" *NJAF* 6:68–71.
Coladonato, Milo (1991) "*Juglans nigra*" 1–11.
Esser, Lora. (1993) "*Juglans californica*" 1–11.
Pavek, Diane S. (1993) "*Juglans major*" 1–13.
Tirmenstein, D.S (1990) "*Juglans microcarpa*" 1–11.
Website: http://www.treeguide.com/naspecies.asp?treeid=junigr1: printed Aug. 30, 2001: pp. 1–11.
Website: http://virual.clemson.edu/groups/FieldOps/Cgs/walnut.htm: printed Aug. 30, 2001: pp. 1–3.
Woeste, K., et. al. (2002) "Thirty Polymorphic Nuclear Microsatellite Loci From Black Walnut" *The Journal of Heredity* 93(1):58–60.

*Primary Examiner*—Kent Bell
(74) *Attorney, Agent, or Firm*—Alice O. Martin; Barnes & Thornburg LLP

(57) ABSTRACT

A new and distinct cultivar of black walnut tree (*Juglans nigra* L.) which is distinctly characterized by extremely rapid growth rate, excellent central stem tendency, and excellent straightness thereby producing good timber qualities. The culture has good resistance to anthracnose leaf disease. This new variety of black walnut trees was discovered by the applicant near South Raub, Tippecanoe County, Ind. in a black walnut planting from previously selected trees for outstanding timber production potential. This selection has been designated as BW510, a seedling progeny of unpatented BW95 in records maintained by the applicant on the performance of this selection, and grafts made from the selection and will be known henceforth as 'Beineke 13'.

3 Drawing Sheets

Latin name of the genus and species: *Juglans nigra* L.
Variety denomination: 'Beineke 13'.

BACKGROUND OF THE INVENTION

This new variety of black walnut tree (*Juglans nigra* L.) was discovered by the applicant near South Raub, Tippecanoe County, Ind. in a black walnut planting of seedling progeny from previously selected trees for outstanding timber producing potential. This selection has been designated as BW510, a seedling progeny of BW95, unpatented, in records maintained by the applicant on the performance of this selection, and grafts made from the selection and will be known henceforth as 'Beinke 13'. The male parent is unknown, as is generally the case with black walnut trees. (Beineke, 1989)

SUMMARY OF THE INVENTION

A new and distinct cultivar of black walnut tree (*Juglans nigra* L.) which is distinctly characterized by extremely rapid growth rate, excellent strong central stem tendency, and excellent straightness, thereby producing excellent timber qualities, the trait of commercial interest and good resistance to anthracnose leaf disease. 'Beineke 13' was 9 years old when described at a location near South Raub, Ind.

After the original clone was selected, and assigned an identity number of BW510 the aforesaid tree was reproduced by collecting scions from it and grafting these onto common black walnut rootstocks at West Point, Ind. These asexual reproductions ran true to the originally discovered tree and to each other in all respects. A growth comparison between BW95 and 'Beineke 13' could not be made at this site because BW95 was not planted at South Raub or West Point and the original tree was cut down. However, since form is not site dependent, old form ratings of BW95 on other sites can be used.

Color values used were from the Munsell Color Chart for Plant Tissues. However, color is too dependent on weather conditions and fertilization to be consistent or dictinctive. For example, leaves can be made a deeper green by applying nitrogen. Walnut tree leaves turn yellow as the season progresses, especially if there is a lack of rainfall. As black walnut meats dry, they become darker. Simply being on the ground for a week causes the outer shell to darken. Bark color involves many shades of gray through brown and black.

'Beineke 13' is hardy in USDA zones 4,5,6,7, and 8.

BOTANICAL DESCRIPTION OF THE PLANTS

Figure 1:
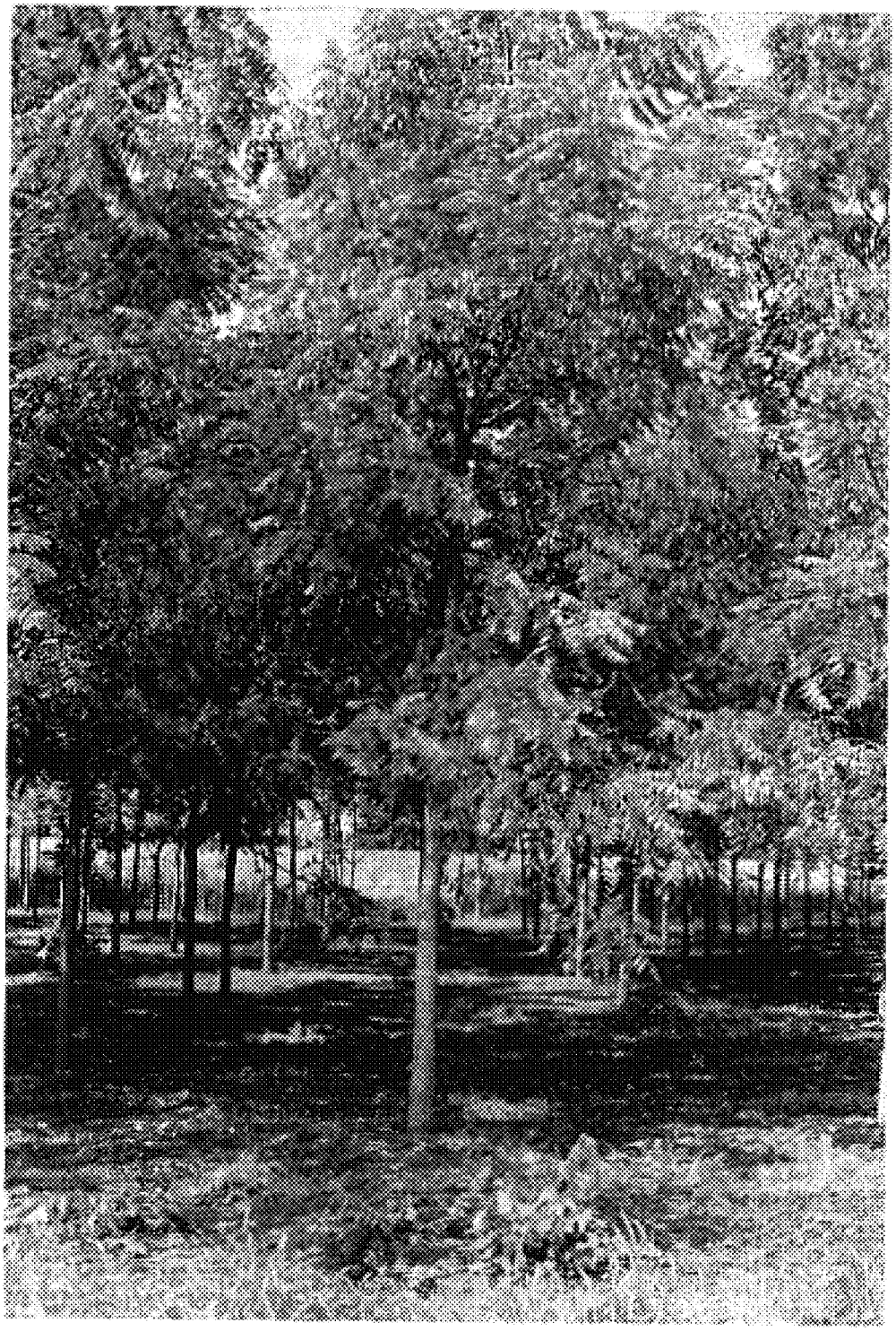
FIG. 1 is a photograph showing the timber form of 'Beineke 13'.
Figure 2:
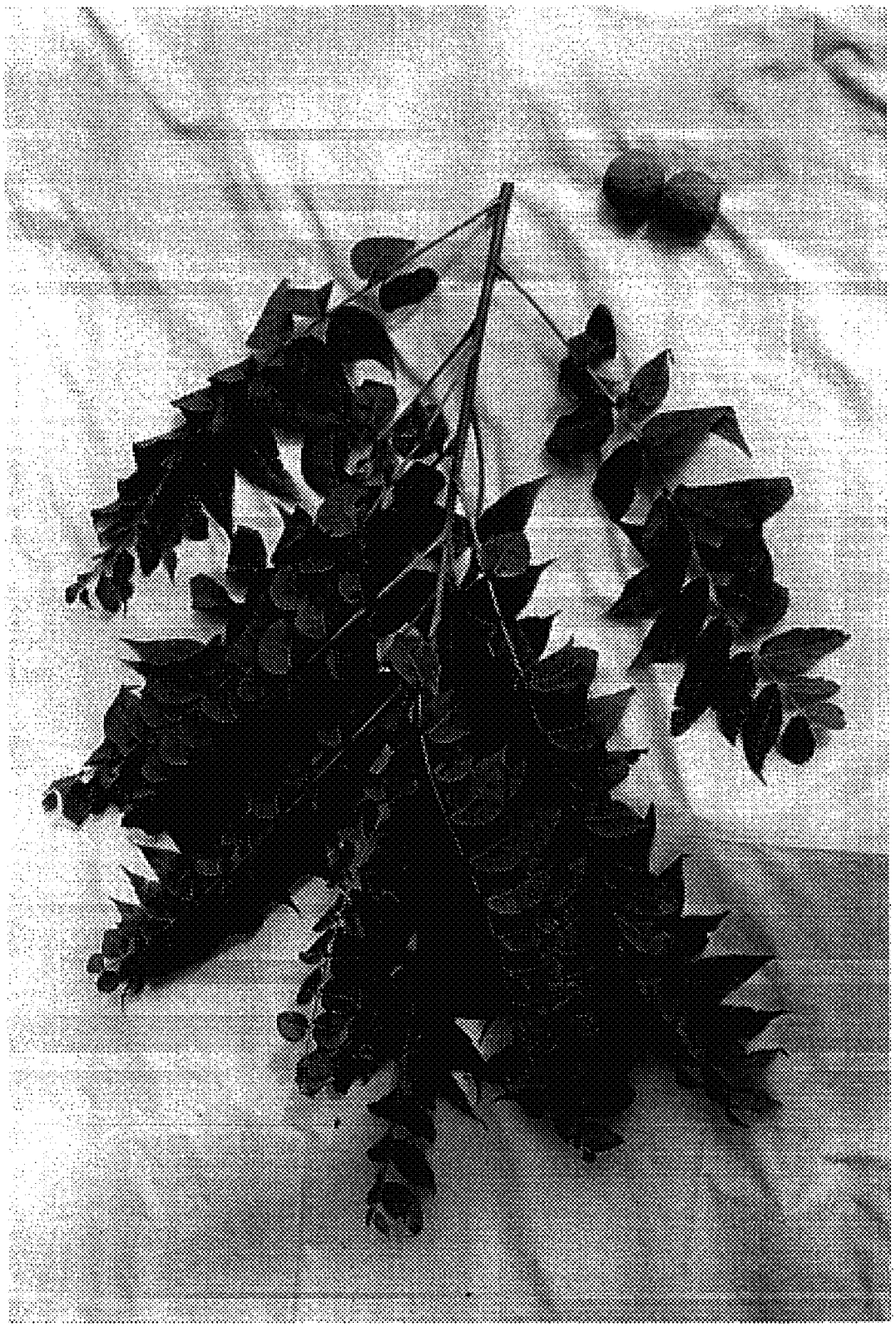
FIG. 2 is a photograph showing the leaves of 'Beineke 13'.

The botanical details of this new and distinct variety of walnut tree are as follows:

Tree:

*Size.*—Large, 35 ft. at 9 years; crown diameter of 15 ft.

*Vigor.*—Vigorous.

*Growth rate.*—Very rapid, 15% larger in diameter than the average of 'Purdue 1' (U.S. Plant Pat. No. 4,543) grafts, planted the same year on the same land. Diameter growth rate (at 4½ above the ground) averages 0.78 inches per year over 9 years, was 7.0 inches at 9 years.

*Form.*—Excellent timber form, 59% better than average of the entire planting and the same as 'Purdue 1' (U.S. Plant Pat. No. 4,543). Stem form was obtained by subjectively rating the straightness of the main stem on a scale of 1 to 5 with 1 representing a perfectly straight stem; 2, a slight crook or deviation of the central stem; 3, about average straightness; 4, several severe crooks or a single fork; and, 5, a very crooked, forked and/or leaning central stem. 'Beineke 13' averages 1 on the 1 to 5 scale while parent BW95 averages 3 on another site.

Branches: Diameter depends on age and size of tree, varies from ½" to 12", bark color varies from grays to browns.

Leaves:

*Compound leaves.*—Size — Large; average length — 22.30"; width 9.93". Compared to 'Purdue 1' (U.S. Plant Pat. No. 4,543), the leaves of 'Beineke 13' are much longer. 'Beineke 13' averages 7.8 inches longer than 'Purdue 1'.

*Leaflets.*—Size — Large; average length — 5.08"; average width 2.20" average number of leaflets — 21.4 — lanceolate; acutely pointed. The leaflets of 'Beineke 13' are 0.71 inches longer and 0.7 inches wider than leaflets of 'Purdue 1'. 'Beineke 13' has an unusually large leaflet compared to most other black walnuts. 'Beineke 13' averages 1.2 more leaflets than 'Purdue 1'. Leaflet number appears to be a consistent trait within tree and year to year.

*Thickness.*—Thin; Texture — smooth; Margin — serrated; Petioles — short; Color — Topside — dark green (5GY3/4 by the Munsell Color Chart for Plant Tissues); Underside — light green (5GY5/4 on the Munsell Color Chart for Plant Tissues).

*Anthracnose resistance.*—Good.

Nut:

*Size.*—Large; average length — 1.42"; average diameter in suture plane — 1.22"; average diameter cheek to cheek — 1.42".

*Uniformity of size.*—Not much variation.

Figure 3:
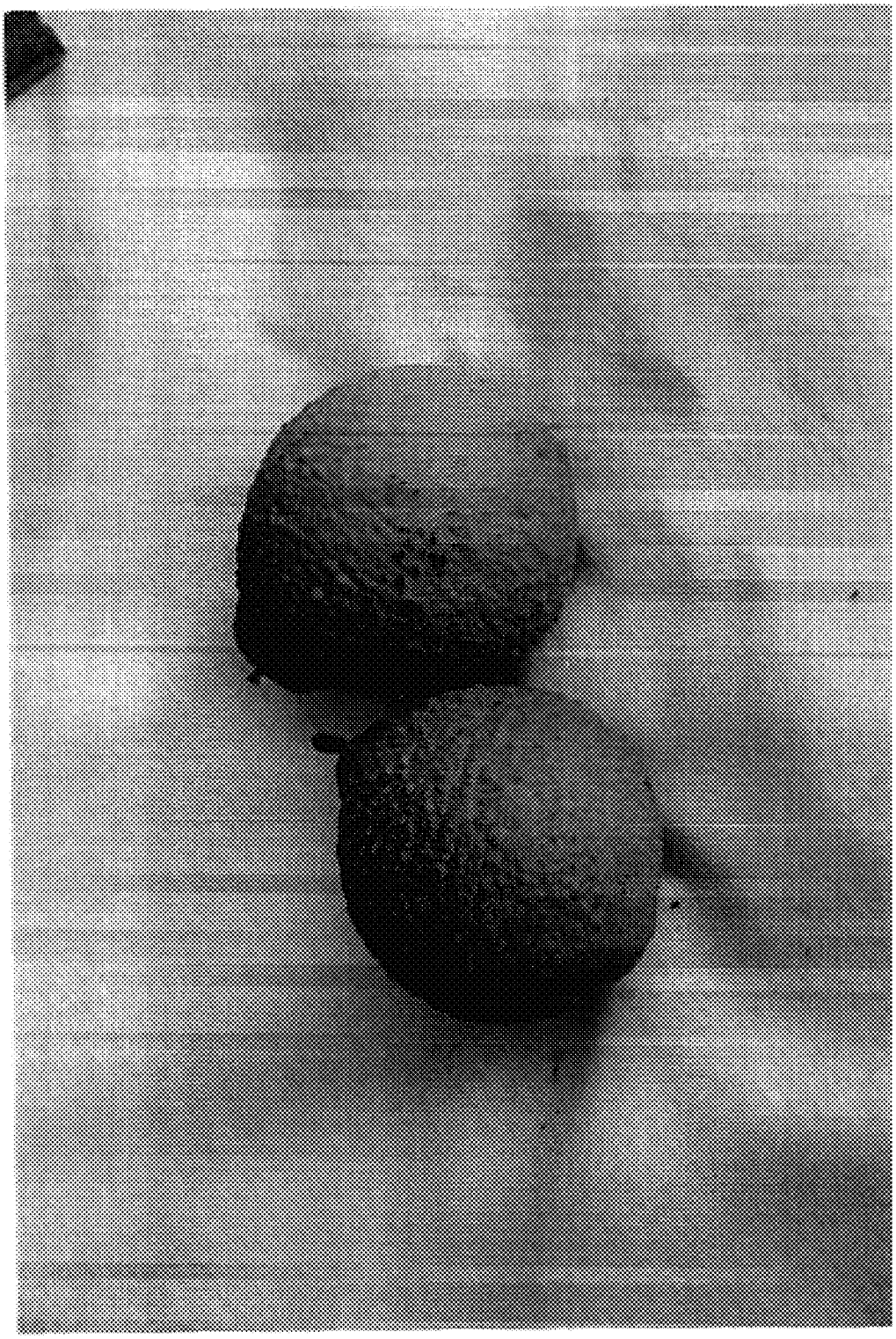
FIG. 3 is a photograph showing the nuts of 'Beineke 13'.

*Form.*—Somewhat heart-shaped. See FIG. 3.

*Blossom end.*—Pointed.

*Basal end.*—Flat.

*Thickness of shell.*—Thick.

*Ridges.*—Rounded.

*Color.*—Mottled, 5YR3/2 and 2.5YR3/4 by the Munsell Color Chart for Plant Tissues.

The nut of 'Beineke 13' averages 0.33 inches shorter than 'Purdue 1' (U.S. Plant Pat. No. 4,543). 'Beineke 13' average 0.1 inches wider in the suture plane and 0.17 inches wider cheek to cheek than 'Purdue 1'.

Nut with husk:

*Size.*—Very large; average length — 2.68".

*Average suture plane width.*—2.45'; average cheek to cheek width — 2.64".

*Husk thickness.*—1.23 inches.

*Form.*—Rounded; slightly flattened in suture plane; slightly elongated.

*Blossom end.*—Rounded slightly indented.

*Basal end.*—Slightly protruding.

*Surface.*—Very warty, no wax.

*Color.*—Greenish-yellow, 2.5 GY 7/8 by the Munsell Color Chart for Plant Tissues.

The nut in the husk of 'Beineke 13' is 0.18 inches longer than 'Purdue 1' (U.S. Plant Pat. No. 4,543). 'Beineke 13' averages 0.58 inches wider in the suture plane and 0.58 wider cheek to cheek than 'Purdue 1'. The husk of 'Beineke 13' averages 0.48 inches thicker than 'Purdue 3'. 'Beineke 13' produces an unusually large nut and husk. The husk is very thick.

Flowering habit:

*Age at which trees start producing catkins.*—Early, about 3–4 years.

*Number of catkins produced.*—Abundant.

*Age at which trees start producing pistillate flowers.*—Early, about 4–5 years but the flower number varies with the age of the tree.

*Number of pistillate flowers produced by young trees.*—Average.

*Lateral shoots producing pistillate flowers.*—None.

*Number of pistillate flowers per inflorescence.*—2 to 4.

Flower season: Flowers typically in May in Indiana. There are probably 1-million pollen per catkin. Female flowers are about 1/16" long and grow to two "pollen pick up points" which subsequently break apart. Pollen exists as "dust" which is not feasible to quantitate.

Nut crop:

*Bearing.*—Biennial.

*Ripening period.*—Average — early October.

*Evenness of maturity (period between first and last nuts are ready for harvest).*—Even.

*Quality.*—Good.

*Distribution of nuts on tree.*—Throughout.

Since back walnut trees such as 'Beineke 13' are selected for timber production, seasonal productivity is not documented. Growth rate and form are the variables of interest.

GENETIC METHOD OF IDENTIFICATION

DNA "fingerprint" for identification of 'Beineke 13':

DNA was isolated from the leaves of 'Beineke 13'. For purposes of DNA fingerprinting, eleven highly polymorphic loci from a suite of microsatellites developed by Woeste et al. (2002) were chosen. Microsatellites sizes were checked against previously published standards and verified by a second independent analysis. The "fingerprint" is the collection of microsatellite allele sizes at each locus for 'Beineke 13'.

DNA was isolated from the leaves of 4 black walnut trees obtained from Walter Beineke using CTAB extraction buffer (50 mM TRIS-HCL, pH 8.0, 20 mM EDTA, pH 8.0, 0.7 M NaCl, 0.4 M LiCl, 2%SDS, 2% CTAB, nd 1% PVP). After isolation the DNA from each tree was quantified and diluted with nanopure distilled water to a final concentration of 5 ng/microliter. The samples were stored in 96-well plates at −20 degrees C.

For purposes of DNA fingerprinting, eleven highly polymorphic loci from a suite of microsatellites developed by Woeste et al. (2002) were chosen. Amplification of each locus was performed with an MJ Research Tetrad Thermocycler (Waltham, Mass.) using 10 microliter reactions in 96-well plates. The PCR reaction mix contained 2 microliter of the aforementioned black walnut DNA, 5 microliter Sigma Taq ReadyMix (Sigma Aldrich, St. Louis, Mo.), 0.4 microliter of a 20 pmol mixture of forward and reverse fluorescence labeled primer, and 3 microliter PCR grade water supplied with the Sigma ReadyMix. PCR amplification was for 30 cycles of 94 degrees C. for 20 sec, 55 degrees C. for 30 sec, and 72 degrees C. for 1 min. All primers were annealed at 55 degrees C. The products were then held at 4 degrees C. until aliquots could be loaded into 6% Long Ranger (polyacrylamide) denaturing gels (BMA, Rockland, Me.). For each individual 0.5 microliter PCR product was added to 0.75 microliter blue dextran and 0.25 microliter of CXR 350 bp Ladder Standard (Applied Biosystems, Inc., Foster City, Calif.) in a new 96-well plate. The samples were denatured for 2 min at 95degrees C. and loaded onto a CAL96 96-well laminated membrane comb (The Gel Company, San Francisco, Calif.). Electrophoresis was at 3,000 V, 60 mA, 200 Watts, 50degrees C. for 2 hours using an ABI 377 (Perkin Elmer) with 36 cm plates and 0.2 mm spacers. The resulting data was analyzed using ABI's GeneScan 3.1.2 and Genotyper 2.5 (Perkin Elmer). Microsatellite sizes were checked against previously published standards and verified by a second independent analysis. The "fingerprint" is the collection of microsatellite allele sizes at each locus for each tree.

| Locus | Forward (SEQ ID NOS: 1–11) |
|---|---|
| WGA6 | CCATGAAACTTCATGCGTTG |
| WGA24 | TCCCCCTGAAATCTTCTCCT |
| WGA27 | AACCCTACAACGCCTTGATG |
| WGA32 | CTCGGTAAGCCACACCAATT |
| WGA72 | AAACCACCTAAAACCCTGCA |
| WGA89 | ACCCATCTTTCACGTGTGTG |
| WGA90 | CTTGTAATCGCCCTCTGCTC |
| WGA97 | GGAGAGGAAAGGAATCCAAA |
| WGA69 | TTAGTTAGCAAACCCACCCG |
| WGA76 | AGGGCACTCCCTTATGAGGT |
| WGA82 | TGCCGACACTCCTCACTTC |

| Locus | Reverse (SEQ ID NOS: 12–22) |
|---|---|
| WGA6 | CATCCCAAGCGAAGGTTG |
| WGA24 | TTCTCGTGGTGCTTGTTGAG |
| WGA27 | TGCTCAGGCTCCACTTCC |
| WGA32 | ACGGGCAGTGTATGCATGTA |
| WGA72 | ACCCATCCATGATCTTCCAA |
| WGA89 | TGCCTAATTAGCAATTTCCA |
| WGA90 | TACCTGCAACCCGTTACACA |
| WGA97 | TTGAACAAAAGGCCGTTTTC |
| WGA69 | AGATGCACAGACCAACCCTC |
| WGA76 | CAGTCTCATTCCCTTTTTCC |
| WGA82 | CGTGATGTCGACGGCTG |

The best interpretation of the current data indicates that the probability that any other black walnut tree would have the collection of microsatellite allele sizes listed is estimated to be less than $3\times10^{-14}$.

Sizes (bp) of microsatellites at 11 loci used to fingerprint 'Beineke 13' (2 alleles at each locus).

| Microsatellites used to fingerprint 'Beineke 13': | | | | | | | | | |
|---|---|---|---|---|---|---|---|---|---|
| WGA6 | | WGA24 | | WGA27 | | WGA32 | | WGA72 | |
| 142 | 142 | 236 | 238 | 219 | 223 | 189 | 189 | 147 | 149 |
| WGA89 | | | | WGA90 | | | WGA97 | | |
| 199 | | 199 | | 162 | | 162 | 161 | | 171 |
| WGA69 | | | | WGA76 | | | WGA82 | | |
| 172 | | 176 | | 230 | | 234 | 166 | | 180 |

DOCUMENTS CITED

Beineke, Walter F. (1989) Twenty years of black walnut genetic improvement at Purdue University *North. J. Appl.* For. 6:68–71.

Woeste, K., Burns, R., Rhodes, O., and Michler, C. (2002) Thirty polymorphic nuclear microsatellite loci from black walnut. Journal of Heredity. 93:58–60.

SEQUENCE LISTING

<160> NUMBER OF SEQ ID NOS: 22

<210> SEQ ID NO 1
<211> LENGTH: 20
<212> TYPE: DNA
<213> ORGANISM: Juglans nigra

<400> SEQUENCE: 1 ccatgaaact tcatgcgttg 20

<210> SEQ ID NO 2
<211> LENGTH: 20
<212> TYPE: DNA
<213> ORGANISM: Juglans nigra

<400> SEQUENCE: 2 tccccctgaa atcttctcct 20

<210> SEQ ID NO 3
<211> LENGTH: 20
<212> TYPE: DNA
<213> ORGANISM: Juglans nigra

<400> SEQUENCE: 3 aaccctacaa cgccttgatg 20

<210> SEQ ID NO 4
<211> LENGTH: 20
<212> TYPE: DNA
<213> ORGANISM: Juglans nigra

<400> SEQUENCE: 4 ctcggtaagc cacaccaatt 20

<210> SEQ ID NO 5
<211> LENGTH: 20
<212> TYPE: DNA
<213> ORGANISM: Juglans nigra

<400> SEQUENCE: 5 aaaccaccta aaaccctgca 20

<210> SEQ ID NO 6
<211> LENGTH: 20
<212> TYPE: DNA
<213> ORGANISM: Juglans nigra

<400> SEQUENCE: 6 acccatcttt cacgtgtgtg 20

<210> SEQ ID NO 7
<211> LENGTH: 20
<212> TYPE: DNA
<213> ORGANISM: Juglans nigra

<400> SEQUENCE: 7 cttgtaatcg ccctctgctc 20

<210> SEQ ID NO 8
<211> LENGTH: 20
<212> TYPE: DNA

-continued

<213> ORGANISM: Juglans nigra

<400> SEQUENCE: 8 ggagaggaaa ggaatccaaa 20

<210> SEQ ID NO 9
<211> LENGTH: 20
<212> TYPE: DNA
<213> ORGANISM: Juglans nigra

<400> SEQUENCE: 9 ttagttagca aacccacccg 20

<210> SEQ ID NO 10
<211> LENGTH: 20
<212> TYPE: DNA
<213> ORGANISM: Juglans nigra

<400> SEQUENCE: 10 agggcactcc cttatgaggt 20

<210> SEQ ID NO 11
<211> LENGTH: 19
<212> TYPE: DNA
<213> ORGANISM: Juglans nigra

<400> SEQUENCE: 11 tgccgacact cctcacttc 19

<210> SEQ ID NO 12
<211> LENGTH: 18
<212> TYPE: DNA
<213> ORGANISM: Juglans nigra

<400> SEQUENCE: 12 catcccaagc gaaggttg 18

<210> SEQ ID NO 13
<211> LENGTH: 20
<212> TYPE: DNA
<213> ORGANISM: Juglans nigra

<400> SEQUENCE: 13 ttctcgtggt gcttgttgag 20

<210> SEQ ID NO 14
<211> LENGTH: 18
<212> TYPE: DNA
<213> ORGANISM: Juglans nigra

<400> SEQUENCE: 14 tgctcaggct ccacttcc 18

<210> SEQ ID NO 15
<211> LENGTH: 20
<212> TYPE: DNA
<213> ORGANISM: Juglans nigra

<400> SEQUENCE: 15 acgggcagtg tatgcatgta 20

<210> SEQ ID NO 16

-continued

```
<211> LENGTH: 20
<212> TYPE: DNA
<213> ORGANISM: Juglans nigra

<400> SEQUENCE: 16

acccatccat gatcttccaa                                                20


<210> SEQ ID NO 17
<211> LENGTH: 20
<212> TYPE: DNA
<213> ORGANISM: Juglans nigra

<400> SEQUENCE: 17

tgcctaatta gcaatttcca                                                20


<210> SEQ ID NO 18
<211> LENGTH: 20
<212> TYPE: DNA
<213> ORGANISM: Juglans nigra

<400> SEQUENCE: 18

tacctgcaac ccgttacaca                                                20


<210> SEQ ID NO 19
<211> LENGTH: 20
<212> TYPE: DNA
<213> ORGANISM: Juglans nigra

<400> SEQUENCE: 19

ttgaacaaaa ggccgttttc                                                20


<210> SEQ ID NO 20
<211> LENGTH: 20
<212> TYPE: DNA
<213> ORGANISM: Juglans nigra

<400> SEQUENCE: 20

agatgcacag accaaccctc                                                20


<210> SEQ ID NO 21
<211> LENGTH: 20
<212> TYPE: DNA
<213> ORGANISM: Juglans nigra

<400> SEQUENCE: 21

cagtctcatt ccctttttcc                                                20


<210> SEQ ID NO 22
<211> LENGTH: 18
<212> TYPE: DNA
<213> ORGANISM: Juglans nigra

<400> SEQUENCE: 22

cgtgatgtac gacggctg                                                  18
```

I claim:

1. A new and distinct variety of black walnut tree named ‘Beineke 13’ substantially as illustrated and described, which has excellent timber quality, extremely rapid growth rate, and excellent central stem tendency.

* * * * *